United States Patent
Smith et al.

(10) Patent No.: US 12,201,284 B2
(45) Date of Patent: Jan. 21, 2025

(54) MEDICAL SEAL ASSEMBLIES AND METHODS OF USING THE SAME

(71) Applicant: Boston Scientific Scimed, Inc., Maple Grove, MN (US)

(72) Inventors: Amanda Lynn Smith, Boston, MA (US); Joseph W. King, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 367 days.

(21) Appl. No.: 17/323,841

(22) Filed: May 18, 2021

(65) Prior Publication Data

US 2021/0361147 A1 Nov. 25, 2021

Related U.S. Application Data

(60) Provisional application No. 63/027,223, filed on May 19, 2020.

(51) Int. Cl.
*A61B 1/00* (2006.01)
*A61B 17/00* (2006.01)
*A61M 5/145* (2006.01)

(52) U.S. Cl.
CPC ...... *A61B 17/00491* (2013.01); *A61B 1/0008* (2013.01); *A61B 1/00137* (2013.01); *A61M 5/1452* (2013.01); *A61M 2205/197* (2013.01)

(58) Field of Classification Search
CPC .............. A61B 1/0008; A61B 1/00087; A61B 1/00089; A61B 1/00101; A61B 1/015; A61B 1/041; A61M 5/14566; A61M 5/1456; A61M 5/14216
See application file for complete search history.

(56) References Cited

U.S. PATENT DOCUMENTS

| | | | |
|---|---|---|---|
| 2010/0010302 A1* | 1/2010 | Hadani | A61B 1/00101 600/173 |
| 2010/0114059 A1* | 5/2010 | Hiniduma-Lokuge | A61M 5/1413 604/246 |
| 2011/0054326 A1* | 3/2011 | Barnett | A61B 1/00094 600/101 |
| 2011/0068144 A1 | 3/2011 | Krehel | |
| 2011/0270184 A1* | 11/2011 | Gunday | A61M 25/0084 604/131 |
| 2017/0258299 A1* | 9/2017 | Aikawa | A61B 1/00089 |
| 2019/0150964 A1 | 5/2019 | Bargon et al. | |

OTHER PUBLICATIONS

International Search Report and Written Opinion in International Application No. PCT/US2021/033005, mailed Aug. 25, 2021 (9 pages).

* cited by examiner

*Primary Examiner* — Alexandra L Newton
(74) *Attorney, Agent, or Firm* — Bookoff McAndrews, PLLC

(57) ABSTRACT

A medical device that includes a shaft having a distal end and a cap at the distal end that defines a reservoir for storing a material. The medical device includes a deployment mechanism configured to eject the material from the reservoir, and the deployment mechanism is configured to apply a force to the reservoir. The cap includes a seal or a perforation that is configured to contain the material in the reservoir in the absence of the force applied by the deployment mechanism to the material.

20 Claims, 5 Drawing Sheets

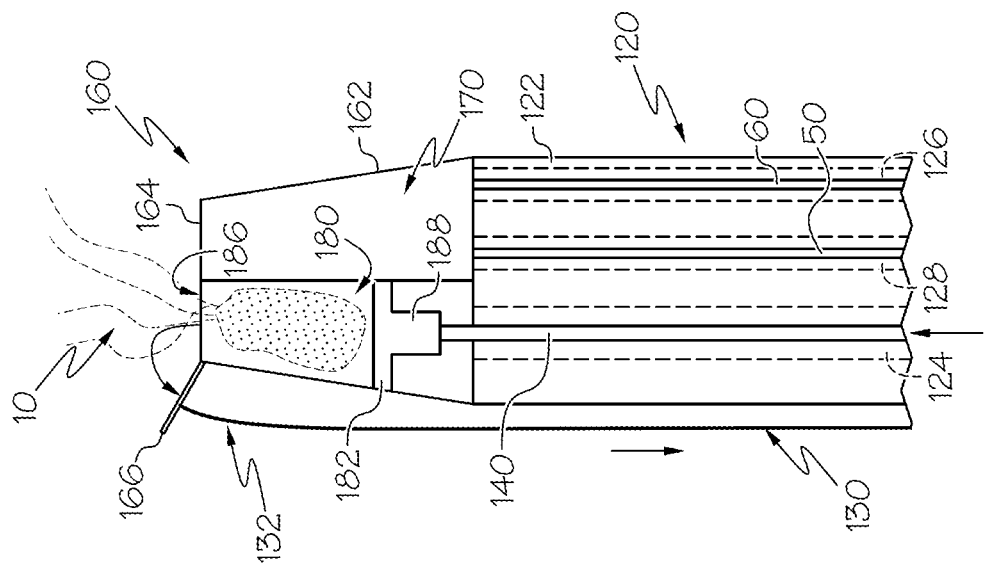
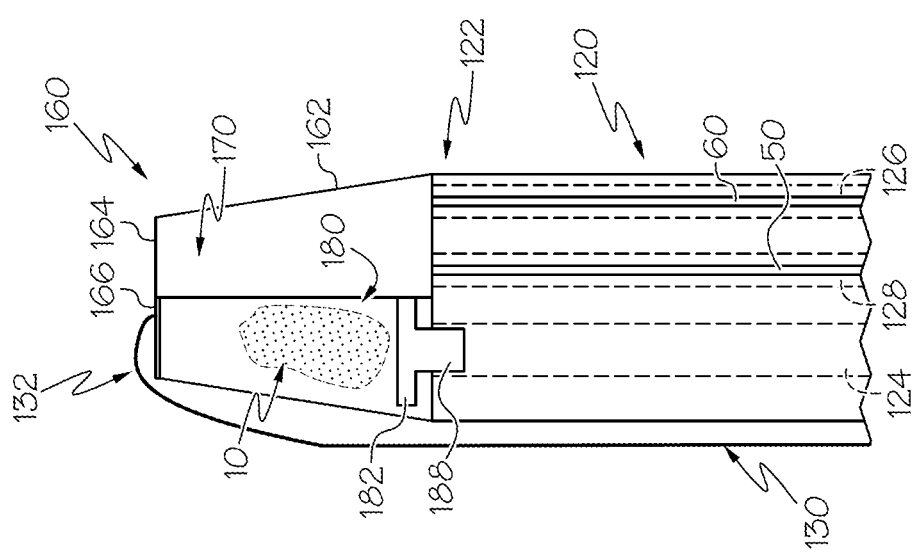

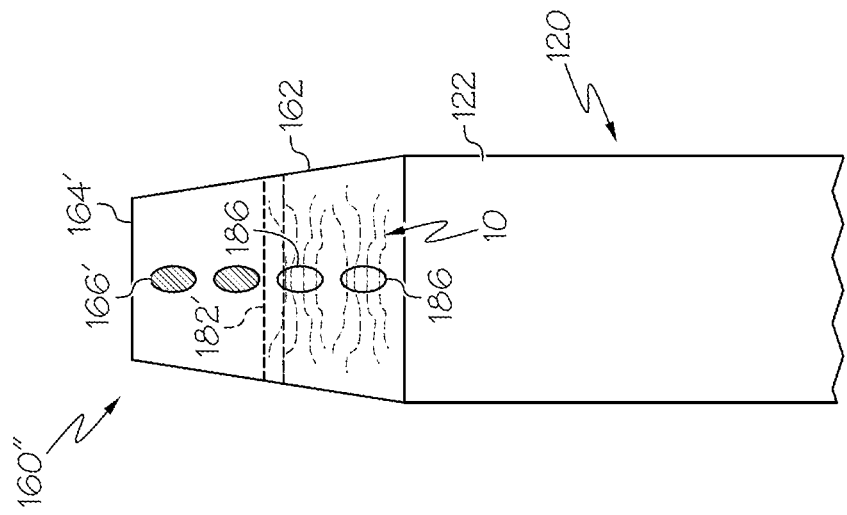
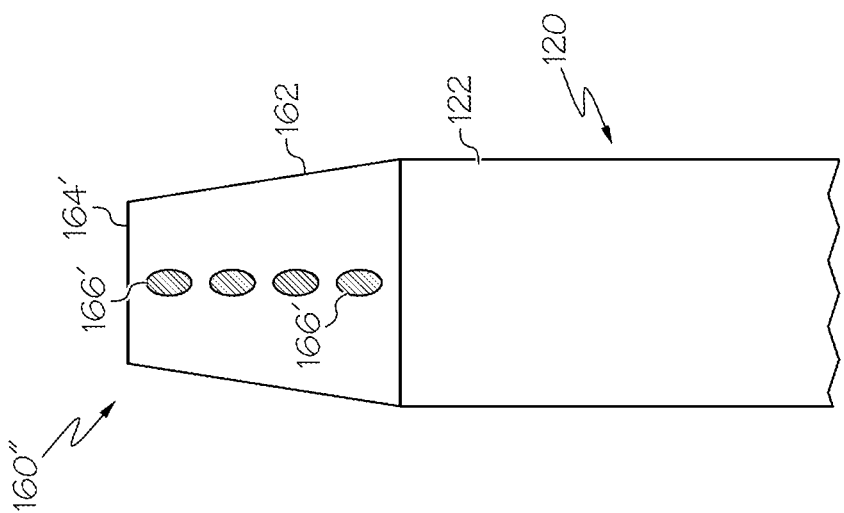

MEDICAL SEAL ASSEMBLIES AND METHODS OF USING THE SAME

CROSS-REFERENCE TO RELATED APPLICATIONS

This application claims the benefit of priority from U.S. Provisional Application No. 63/027,223, filed on May 19, 2020, which is incorporated by reference herein in its entirety.

TECHNICAL FIELD

Various aspects of the disclosure relate generally to medical seal systems, devices, and related methods. Examples of the disclosure relate to systems, devices, and related methods for providing a deployable seal on a medical instrument, among other aspects.

BACKGROUND

Technological developments have given users of medical systems, devices, and methods, the ability to conduct increasingly complex procedures on subjects. One challenge in the field of minimally invasive surgeries is associated with promoting healing by delivering a material (e.g., adhesive, therapeutic agent, regenerative substance, etc.) to internally-treated areas.

SUMMARY

Aspects of the disclosure relate to, among other things, systems, devices, and methods for providing a medical device capable of delivering and releasing a healing material to a subject, among other aspects. Each of the aspects disclosed herein may include one or more of the features described in connection with any of the other disclosed aspects.

According to an example, a medical device includes a shaft having a distal end and a cap at the distal end that defines a reservoir for storing a material. The medical device includes a deployment mechanism configured to eject the material from the reservoir, and the deployment mechanism is configured to apply a force to the reservoir. The cap includes a seal or a perforation that is configured to contain the material in the reservoir in the absence of the force applied by the deployment mechanism to the material.

Any of the medical devices described herein may include one or more of the following features. The deployment mechanism includes a movable floor that is distal of the distal end of the shaft. The deployment mechanism further includes a movable rod disposed within the shaft and extendable from the distal end. The movable rod is configured to push the movable floor distally away from the distal end of the shaft to eject the material from the reservoir. The shaft includes a lumen and the distal end includes an opening, wherein the movable rod is configured to extend through the opening. The movable floor includes a notch that is received within the opening and is configured to align the movable floor with the movable rod. The deployment mechanism includes a source of pressurized medium, wherein the pressurized medium is configured to be delivered through the shaft from the pressurized medium source. The seal includes a movable cover coupled to the cap, wherein the movable cover is configured to move to form an opening through which the material is able to exit the cap. The medical device may include an actuator coupled to the movable cover, wherein actuation of the actuator is configured to move the movable cover to form the opening. The actuator is configured to move the movable cover in response to receiving a proximal pulling force. The actuator includes a wire, a cable, or a thread. The perforation is configured to expand and form an opening through which the material can exit the cap, wherein the opening has a greater size than the perforation. The cap includes a breakable portion adjacent to the perforation, wherein the breakable portion is configured to break in response to expansion of the perforation and form an enlarged opening through which the material is able to exit the cap. An outer surface of the cap includes a biodegradable material that is configured to degrade within seconds or minutes of contact with tissue. The cap includes a plurality of perforations staggered in series and in a longitudinal configuration relative to one another.

According to another example, a medical device includes a cap configured to be attached to a distal end of a scope, wherein the cap defines a reservoir for storing a material. The cap includes a removable seal configured to expose the reservoir and the material upon removal of the seal from a remainder of the cap. The cap includes a deployment mechanism configured to eject the material from the reservoir. The deployment mechanism is configured to generate a positive pressure within the reservoir.

Any of the medical devices described herein may include one or more of the following features. The removable seal is formed of biodegradable material such that the removable seal is configured to degrade upon exposure to a target site for a predetermined duration.

According to another example, a cap configured to be attached to a distal end of a scope, wherein the cap defines a reservoir for storing a material. The cap includes a plurality of perforations configured to expand and allow the material to exit the cap, and a deployment mechanism configured to eject the material from the reservoir via the plurality of perforations. The deployment mechanism is configured to apply a force to the material within the reservoir.

Any of the medical devices described herein may include one or more of the following features. The plurality of perforations is configured to contain the material within the cap when the deployment mechanism is in an initial position. The plurality of perforations is configured to expand in response to the deployment mechanism extending distally into the cap and toward the plurality of perforations.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIG. 3A is a partial side view of the medical instrument of FIG. 1 including the cap assembly in the sealed state, according to aspects of this disclosure;

FIG. 3B is a partial side view of the medical instrument of FIG. 1 including the cap assembly in the unsealed state, according to aspects of this disclosure;

FIG. 5A is a partial side view of another exemplary medical instrument including a cap assembly in an expanded state, according to aspects of this disclosure; and FIG. 5B is a partial side view of the medical instrument of FIG. 5A with the cap assembly in an expanded state, according to aspects of this disclosure.

DETAILED DESCRIPTION

Examples of the disclosure include systems, devices, and methods for providing a medical instrument storing a material, delivering the medical instrument to a target treatment site within a subject (e.g., a patient), and removing a seal to deliver the material to the target treatment site.

As used herein, the term "distal" refers to a portion farthest away from a user when introducing a device into a patient and the term "proximal" refers to a portion closest to the user when placing the device into the subject. The terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices. Reference will now be made in detail to examples of the disclosure described above and illustrated in the accompanying drawings. Wherever possible, the same reference numbers will be used throughout the drawings to refer to the same or like parts.

Figure 1:
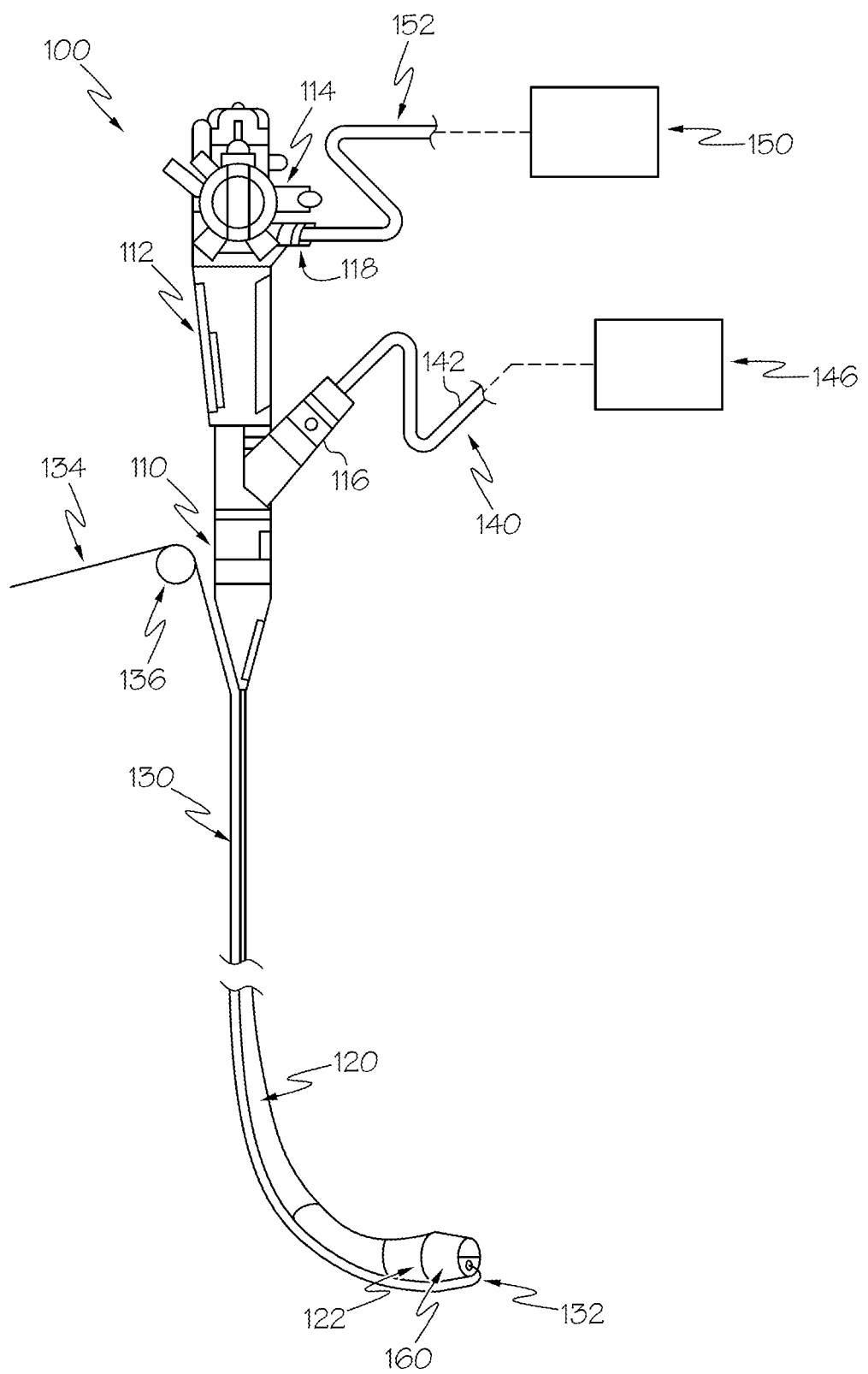
FIG. 1 is a perspective view of an exemplary medical instrument including a cap assembly, according to aspects of this disclosure.

FIG. 1 shows an exemplary medical system 100 in accordance with an example of this disclosure. Medical system 100 may include a medical instrument 110. For example, medical instrument 110 may include an endoscope, duodenoscope, gastroscope, colonoscope, ureteroscope, bronchoscope, and/or various other delivery systems. Medical instrument 110 may include a handle 112, at least one actuator 114, one or more ports 116, 118, and a shaft 120. Handle 112 may be defined by a proximal end including actuator 114 and a distal end including shaft 120 extending distally therefrom. The one or more ports 116, 118 may extend outwardly from handle 112 and be configured to facilitate receipt of one or more devices into medical instrument 110. It should be appreciated that medical instrument 110 may include additional and/or fewer ports 116, 118 than those shown and described herein.

Handle 112 may have one or more lumens (not shown) that communicate with a lumen(s) of one or more other components of medical instrument 110. The one or more ports 116, 118 may open into the one or more lumens of handle 112 and are sized and shaped to receive one or more devices therethrough, such as, for example, a mechanical rod 140, a tube 152, and more. Shaft 120 may include a tube that is sufficiently flexible such that shaft 120 is configured to selectively bend, rotate, and/or twist when being inserted into and/or through a subject's tortuous anatomy to a target treatment site.

Although not shown, it should be understood that shaft 120 may have one or more lumens extending therethrough that include, for example, a working lumen for receiving instruments, such as mechanical rod 140 received in medical instrument 110 at port 116. Shaft 120 may further include a fluid lumen for delivering a fluid, such as, for example, from a pressurized medium source 150 fluidly coupled to medical instrument 110 at port 118 via tube 152. Shaft 120 also may include an additional fluid lumen for conveying fluid away from the distal end of medical instrument 110. It should be appreciated that medical system 100 may include various other suitable devices than those shown and described herein.

In other examples, shaft 120 may include additional lumens such as a control wire lumen for receiving one or more control wires for actuating one or more distal parts/tools (e.g., an articulation joint, an elevator, etc.), an illumination lumen for receiving at least a portion of an illumination assembly (FIGS. 3A-3B), and/or an imaging lumen for receiving at least a portion of an imaging assembly (FIGS. 3A-3B). Shaft 120 may further include a distal end 122 defining one or more openings that are in communication with the one or more lumens of shaft 120.

Still referring to FIG. 1, mechanical rod 140 may be a plunger having an elongated body 142 that is substantially flexible and defined between a distal end (not shown in FIG. 1) and a proximal end 142. In some examples, mechanical rod 140 may be a deployment mechanism including a handle 146 adjacent to proximal end 142 for selectively controlling a movement of mechanical rod 140 through the working lumen of shaft 120. Pressurized medium source 150 may be another deployment mechanism and may include a hydraulic system, a pneumatic system, and/or the like. For example, pressurized medium source 150 may be configured to store and deliver a pressurized medium through the fluid lumen of shaft 120. In some examples, the pressurized medium may include compressed air, fluid, liquid, gas, and the like.

Medical system 100 may further include an actuator 130 having a longitudinal length defined by a distal end 132 and a proximal end 134. Actuator 130 may have a substantially flexible body and may include, for example, a cable, a thread, a string, a wire, a bundle of any of the aforementioned elements, and the like. As described in further detail below, actuator 130 may be disposed adjacent to medical instrument 110 during use in a procedure with proximal end 134 positioned adjacent to handle 112, distal end 132 positioned adjacent to distal end 122, and an elongated body of actuator 130 disposed alongside shaft 120.

Still referring to FIG. 1, proximal end 134 may be configured to facilitate a selective control of actuator 130. In some embodiments, actuator 130 may be coupled to an indexing mechanism 136 configured to facilitate movement of actuator 130 relative to the working lumen. For example, indexing mechanism 136 may include a rotatable wheel, a knob, a lever, a button, a switch, etc. Actuator 130 may be coupled to indexing mechanism 136 along proximal end 134 such that actuation of indexing mechanism 136 may cause actuator 130 to move by pulling actuator 130 proximally about indexing mechanism 136. In other embodiments, indexing mechanism 136 and/or actuator 130 may be omitted entirely.

Medical system 100 may further include a cap assembly 160 disposed on distal end 122. Cap assembly 160 may be configured to seal and/or enclose one or more openings along distal end 122, such as, for example, one or more openings corresponding to the one or more lumens of shaft 120. As described in further detail herein, cap assembly 160 may be further configured to deliver one or more materials from medical instrument 110, such as, for example, to a target treatment site within a subject during a procedure. In the example, actuator 130 may extend distally relative to distal end 122 and distal end 132 may be fastened to an outer and distally-facing surface of cap assembly 160 (e.g., via an adhesive, a knot, etc.).

Figure 2A:
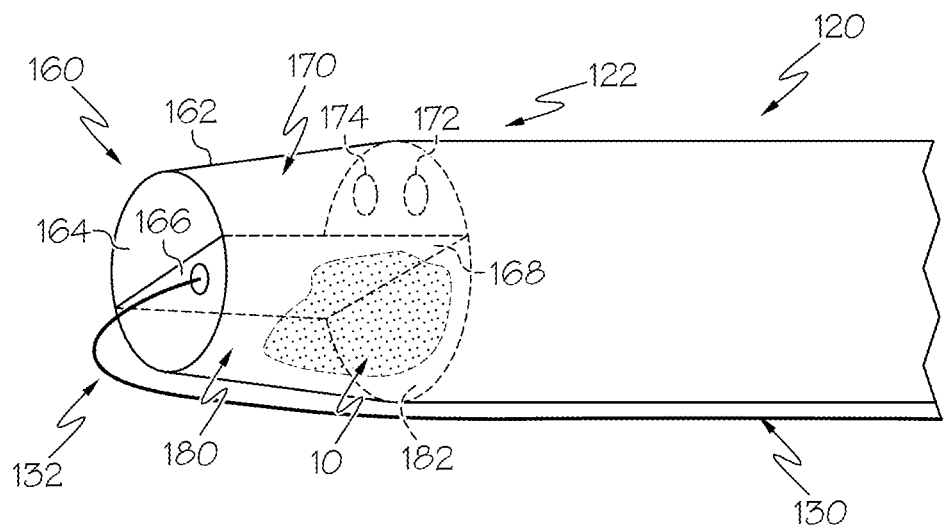
FIG. 2A is a partial perspective view of the medical instrument of FIG. 1 with the cap assembly in a sealed state, according to aspects of this disclosure.

Referring now to FIG. 2A, cap assembly 160 is depicted in a partially transparent manner such that a reservoir (e.g., compartment) defined by cap assembly 160 is shown. For example, cap assembly 160 may include an outer body 162, a distal face 164, a removable cover 166, and a partition wall 168. Outer body 162 may include various suitable sizes and/or shapes that may adequately enclose distal end 122 of shaft 120. Distal face 164 and removable cover 166 may be positioned at a distal end of outer body 162, opposite of a proximal end secured to distal end 122 of shaft 120. In some embodiments, distal face 164 is not removable or is otherwise fixed to outer body 162.

Accordingly, distal face 164 and removable cover 166 may be sized and/or shaped to collectively define a distal end of cap assembly 160. In other examples, removable cover 166 may be positioned along various other portions of outer body 162 such that a non-removable and/or fixed distal face 164 may define an entirety of the distal end. In the example shown, the distal end of outer body 162 may have a circular shape and each of distal face 164 and seal assembly 160 may have a semicircular shape. As described further below, distal face 164 and removable cover 166 may be positioned on the distal end along opposing sides of partition wall 168.

Still referring to FIG. 2A, distal face 164 may be formed of a substantially transparent material such that one or more devices disposed within outer body 162 may be visible through distal face 164, and so that a user may be able to visualize a field of view distal of outer body 162, using, e.g., imaging equipment located at distal end 122 of shaft 120. Removable cover 166 may be disposed over an opening 186 (FIG. 2B) on the distal end of outer body 162. For example, removable cover 166 may be securely coupled over opening 186 on the distal end by various suitable mechanisms (e.g., an adhesive, a mechanical engagement, etc.). In the example, removable cover 166 may include a flexible tab that is selectively removable from opening 186 in response to an application of force applied thereto. In other examples, removable cover 166 may be coupled to outer body 162 by a hinge bracket or a living hinge.

Partition wall 168 may be disposed within cap assembly 160 and extend through an inner cavity defined by outer body 162. In the example, partition wall 168 may divide the inner cavity and at least partially define and separate reservoirs 170, 180 within outer body 162. Accordingly, partition wall 168 may separate a visualization reservoir/space 170 from a material reservoir 180 such that one or more devices of medical instrument 110 and/or cap assembly 160 in visualization reservoir 170 may be shielded and/or isolated from one or more devices in material reservoir 180, and vice versa. As briefly described above, shaft 120 may include one or more openings 170, 172 on distal end 122. It should be understood that the one or more lumens of shaft 120 may terminate at openings 170, 172. In yet other examples, cap assembly 160 does not cover the entire distal face of shaft 120, so that imaging devices remain unobstructed.

In some examples, medical system 100 may include an illumination device (not shown) and an imaging device (not shown). The devices may be coupled to medical instrument 110 via the one or more ports 116, 118. The illumination device (e.g., optical fiber) and the imaging device (e.g., camera, sensor, etc.) may be received through respective lumens of handle 112 and shaft 120. In the example, the illumination device may be positioned at distal end 122 in a first opening 172; and the imaging device may be positioned at distal end 122 in a second opening 174. It should be understood that distal end 122 may include additional and/or fewer openings for facilitating access to one or more lumens in shaft 120.

Still referring to FIG. 2A, first opening 172 and second opening 174 may be disposed within visualization reservoir 170 when cap assembly 160 is attached to distal end 122. Accordingly, distal face 164 may be longitudinally aligned with openings 172, 174 such that the illumination device may be configured to provide lighting distally relative to cap assembly 160 through transparent distal face 164, and the imaging device may be configured to capture images of a distal position from cap assembly 160 through distal face 164.

Cap assembly 160 may further include a movable floor 182 disposed within material reservoir 180 and having a top surface and a bottom surface. The top surface of movable floor 182 may be a distally-facing surface that faces removable cover 166, and defines an interface for receiving one or more materials 10 thereon. In the example, material reservoir 180 may be prefilled with material 10 such that material 10 may be included between removable cover 166 and movable floor 182 prior to an assembly of cap assembly 160 onto shaft 120. In some examples, material 10 may include an adhesive, a therapeutic agent, a regenerative substance, and/or various other materials for delivery by medical instrument 10 to a subject.

Still referring to FIG. 2A, movable floor 182 may be a deployment mechanism configured to act as a mechanical piston configured to translate within material reservoir 180 and relative to outer body 162. As described in detail below, movable floor 182 may be movable in response to an actuation of one or more other components of medical system 100, such as, for example, mechanical rod 140 (FIG. 1). In some embodiments, movable floor 182 is not removable from cap assembly 160, such as, for example, prior to assembling cap assembly 160 onto medical instrument 110. In this instance, material 10 may be maintained in material reservoir 180 and inhibited or prevented from being released due to movable floor 182 falling proximally outward from outer body 162. Movable floor 182 could be, for example, a coated rubber piston similar to those used in syringes and injection devices. Movable floor 182 could include one or more features that prohibit proximal movement relative to outer body 162, and/or outer body 162 could include one or more stops extending radially inward and positioned proximal of movable floor 172 that blocks or prevents proximal movement of movable floor 182.

Figure 2B:
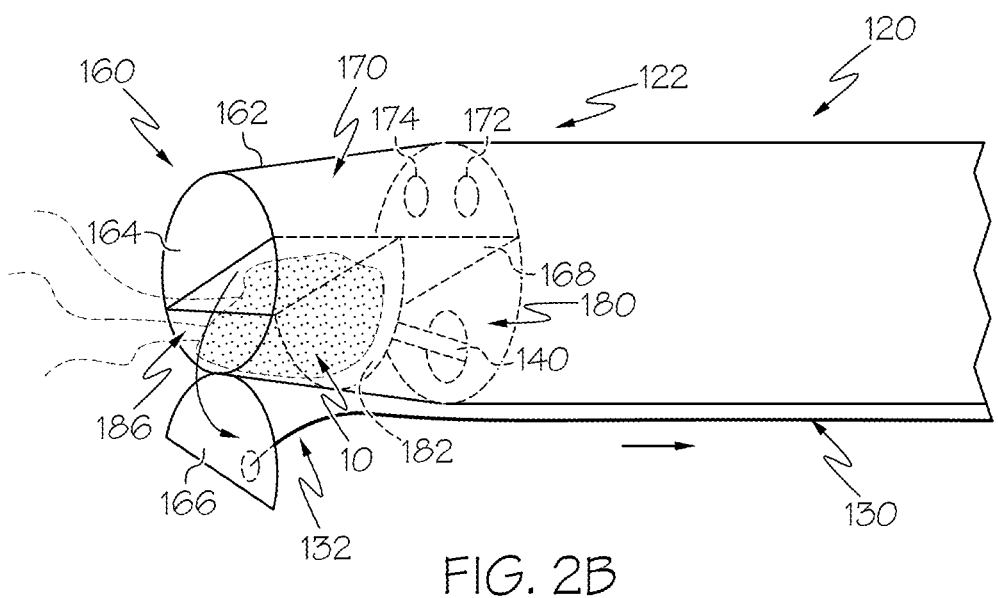
FIG. 2B is a partial perspective view of the medical instrument of FIG. 1 with the cap assembly in an unsealed state, according to aspects of this disclosure.

Actuator 130 may be attached to cap assembly 160 along removable cover 166. For example, distal end 132 may be secured to an exterior of removable cover 166 (i.e. opposite of an interior facing and disposed within material reservoir 180) and actuator 130 may be configured to apply a distal (pulling) force thereto to remove removable cover 166 from outer body 162. In this instance, actuator 130 may expose opening 186 (FIG. 2B). As described further below, actuator 130 may apply the force to removable cover 166 in response to a proximal translation of actuator 130 at proximal end 132.

Referring back to FIG. 1 and according to an exemplary method of using medical system 100 during a procedure, medical instrument 110 may receive cap assembly 160 by attaching outer body 162 to distal end 122. Cap assembly 160 may be preloaded with material 10 within material reservoir 180 (FIG. 2A), with material 10 including a substance for delivery to a target treatment site within a subject (e.g., a patient). Alternatively, material 10 could be inserted into material reservoir 180 through opening 186, after cap assembly 160 is coupled to shaft 120. An illumination device and/or an imaging device may be coupled to medical instrument 110 and received through respective lumens of shaft 120 such that the distal ends of the devices are positioned at openings 172, 174. It is further contemplated, however, that the illumination device and/or imaging device are integral with shaft 120.

Referring to FIG. 3A, shaft 120 may be inserted into the subject and navigated to the target treatment site with use of an illumination device 60 (received within an illumination lumen 126 of shaft 120) and an imaging device 50 (received within an imaging lumen 128 of shaft 120). Distal end 122 may be positioned at or adjacent the target treatment site (e.g., a perforation, a wound, stricture formation, etc.) by visually identifying a location of the site with imaging device 50 through distal face 164. Actuator 130 may be actuated by applying a proximally-directed force on actuator 130, to remove removable cover 166 from outer body 162 or otherwise displace removable cover 166 and expose opening 186.

For example, referring back to FIG. 1, actuator 130, and particularly proximal end 134 may be pulled proximally to translate actuator 130 in a proximal direction relative to shaft 120, thereby pulling distal end 132 in a proximal direction. In examples where actuator 130 includes indexing mechanism 136 (FIG. 1), a user may rotate indexing mechanism 136 to wind proximal end 134 about indexing mechanism 136, thereby pulling distal end 132 proximally. It should be appreciated that distal end 132 may be secured to removable cover 166 to an extent such that distal end 132 is fixed to removable cover 166. Accordingly, actuator 130 is configured to pull removable cover 166 away from outer body 162.

Referring now to FIGS. 2B and 3B, removable cover 166 may be at least partially removed from outer body 162 by actuator 130 to expose opening 186. After removable cover 166 is pulled off of or otherwise displaced relative to outer body 162, opening 186 may become unsealed and material reservoir 180 may be exposed. In some embodiments, removable cover 166 may be completely removed from outer body 162 in response to a continued actuation of actuator 130; while in other embodiments, at least a portion of removable cover 166 may remain at least partially fixed to outer body 162 (for example, when removable cover 166 is connected to outer body 162 by a hinge).

Movable floor 182 may be moved distally within material reservoir 180 and relative to outer body 162 in response to mechanical rod 140 moving distally through a working lumen 124 of shaft 120. For example, distal end 122 may include a third opening 184 and working lumen 124 may terminate at third opening 184 (shown only in FIG. 4A). Third opening 184 may be aligned with material reservoir 180 when cap assembly 160 is initially secured to shaft 120.

In some embodiments, cap assembly 160 may include an alignment feature 188 to position movable floor 182 in alignment with third opening 184 during engagement of cap assembly 160 with distal end 122. For example, alignment feature 188 may be a notch, a protrusion, and/or other various members extending proximally and outwardly from a proximal surface of movable floor 182. Alignment feature 188 may be sized and shaped in accordance with a profile of working lumen 124 and/or third opening 184. Accordingly, alignment feature 188 may be configured to extend into working lumen 124 via third opening 184 when cap assembly 160 is coupled to distal end 122.

Actuation of handle 146 may cause mechanical rod 140 to translate through working lumen 124, thereby causing a distal end of mechanical rod 140 to extend distally relative to distal end 122 and outwardly from third opening 184. With movable floor 182 positioned against distal end 122 and alignment feature 188 received within working lumen 124, mechanical rod 140 may be configured to push movable floor 182 towards opening 186 by engaging alignment feature 188.

Accordingly, material 10 may be pushed through material reservoir 180 and ejected outwardly from cap assembly 160 via opening 186. Material 10 may be delivered to the target treatment site when ejected outwardly from material reservoir 180. It should be understood that cap assembly 160 may be configured to inhibit deployment of movable floor 182 outwardly material reservoir 180. For example, opening 186 may be sized and/or shaped relatively smaller than movable floor 182 to inhibit removal of movable floor 182 from material reservoir 180.

In other embodiments, actuator 130 may be omitted entirely such that seal assembly 160 may be removed from outer body 162 in response to mechanical rod 140 moving within containment reservoir 180 and pushing material 10 toward seal assembly 160. Mechanical rod 140 may be operable to generate a pressure against removable cover 166 in response to moving movable floor 182 distally. In this instance, an increase in pressure in a distal direction may cause removable cover 166 to be deployed distally from outer body 162, thereby permitting release of material 10 to the target treatment site. Alternatively, a pressurized medium may be delivered into containment reservoir 180 via third opening 186 to generate the pressure against removable cover 166. In this instance, mechanical rod 140 is omitted and a pressurized medium source may deliver the pressurized medium to the cap assembly 160 to move movable floor 182 distally to deploy removable cover 166 and release material 10.

Removable cover 166 may be formed of a biodegradable and/or bioabsorbable material such that removable cover 166 may be configured to degrade and/or be absorbed by one or more features (e.g., tissue) surrounding cap assembly 160 after deployment. For example, removable cover 166 may be operable to dissolve after a predetermined duration (e.g., minute(s), hour(s), day(s), week(s), etc.) of exposure to the one or more surrounding features at a target treatment site. In other examples, removable cover 166 may be simply received in the target treatment site and naturally passed through the subject (e.g., in a gastrointestinal (GI) tract) until released therefrom.

Figure 4A:
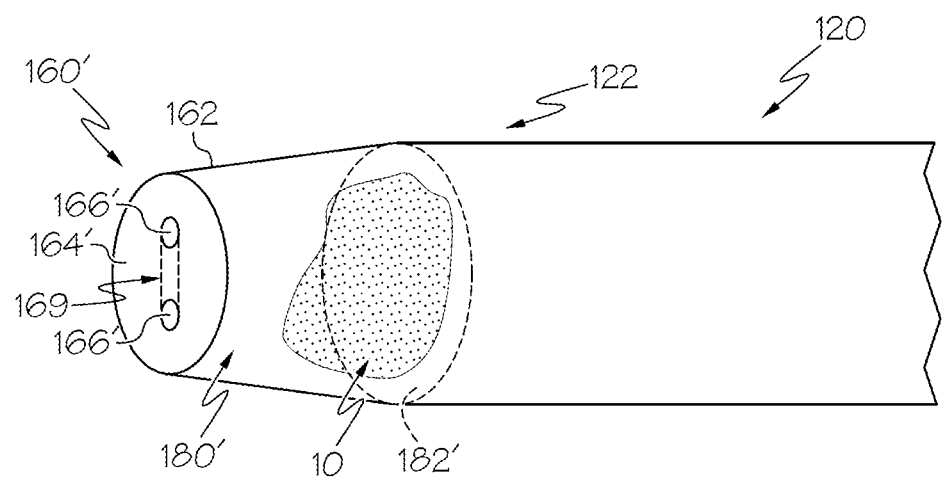
FIG. 4A is a partial perspective view of another exemplary medical instrument including a cap assembly in an unexpanded state, according to aspects of this disclosure.

Referring now to FIG. 4A, another exemplary cap assembly 160' according to an example of this disclosure is shown.

It should be understood that cap assembly 160' may be readily incorporated onto medical instrument 110 in the manner described above. It should also be understood that cap assembly 160' functions substantially similar to cap assembly 160 described above except for the differences explicitly noted herein.

For example, cap assembly 160' may include one or more perforations 166' formed along a distal face 164' of outer body 162. Perforations 166' may include small openings, holes, and/or apertures that are sized, shaped, and configured to facilitate access to cap assembly 160'. As described in detail below, perforations 166' may be configured to retain a material within cap assembly 160' when in a default state (e.g., including a small opening on distal face 164'), and may be further configured to permit release of the material from cap assembly 160' when transitioned to an expanded state forming a relatively larger opening. In the example, cap assembly 160' may include a pair of perforations 166' positioned on distal face 164'. It should be appreciated that additional and/or fewer perforations 166' may be included on various portions of outer body 162 as opposed to those shown and described herein without departing from a scope of this disclosure.

Perforations 166' may include any suitable structure that, in an initial configuration, is configured to help retain material 10 within outer body 162, and, after application of a suitable pressure or force against perforation 166', is configured to break or open, to enable material 10 to be dispensed out of outer body 162. Perforations 166' may include one or more small holes formed in the material by a perforating tool that punctures the outer surface of outer body 162. In some examples, perforations 166' may be formed by a die and punch, or by a laser.

It should be appreciated that a size (e.g., diameter) of perforations 166' may be based on a plurality of factors, including, but not limited to, a thickness of outer body 162, a spacing between each perforations 166', a viscosity of a substance delivered through perforations 166', a desired amount of force required to break outer body 162 and/or perforations 166' to deliver a substance therethrough, and the like. For example, in embodiments in which a substance having a relatively low viscosity (e.g., a liquid) is stored within cap assembly 160', a diameter of perforations 166' may range from about 0.001 inches to about 0.002 inches. By way of further example, in embodiments in which a liquid substance having a relatively high viscosity (e.g., a gel) is stored within cap assembly 160', a diameter of perforations 166' may range from about 0.005 inches to about 0.010 inches. It should be understood that the diameters discussed above are merely exemplary and describe possible size openings that may still maintain the substance within cap assembly 160' despite perforations 166' forming an opening on outer body 162.

It should be further appreciated that a spacing and/or offset of perforations 166' along outer body 162 may be based on a plurality of factors, including, but not limited to, a thickness of outer body 162, a size (e.g., diameter) of perforations 166', a viscosity of a substance delivered through perforations 166', a desired amount of force required to break outer body 162 and/or perforations 166' to deliver a substance therethrough, and the like. For example, perforations 166' may be spaced apart from one another between about 0.001 inches to about 0.050 inches.

In some examples, perforations 166' may open into a larger opening 186 (FIG. 4B) in response to an application of sufficient additional force against each perforation 166'. That is, in response to an initial level of force applied, perforations 166' may enable material 10 to be expelled therethrough, and upon a greater level of force applied, the space surrounding and/or adjacent to perforations 166' may be broken to form an enlarged opening (e.g., opening 186). Thus, increasing a size and/or shape of perforations 166' may enable additional material 10 to be deployed at a faster rate.

Still referring to FIG. 4A, a region of outer body 162 positioned about each perforation 166' may be formed of a material configured to break open, thereby converting perforations 166' into larger openings. For example, perforations 166' may be enlarged in response to mechanical rod 140 moving within containment reservoir 180 and pushing material 10 toward distal face 164'. Thus, mechanical rod 140 may generate a pressure against perforations 166' when moving movable floor 182' distally. The pressure increase may cause perforations 166' to break down and form openings 186 (FIG. 4B), thereby permitting release of material 10 to the target treatment site.

Cap assembly 160' may further include one or more weakened and/or breakable portions 169 along outer body 162. In the example, cap assembly 160' may include at least one weakened portion 169 positioned on distal face 164' between perforations 166'. It should be appreciated that additional and/or fewer weakened portions 169 may be included on various portions of outer body 162 than those shown and described herein without departing from a scope of this disclosure. Weakened portion 169 may be configured to break open an adjacent portion of distal face 164' positioned between perforations 166' as perforations 166' are enlarged as additional force is applied by movable floor 182', thereby increasing a cross-sectional dimension of openings 186 formed along distal face 164'.

As described in greater detail herein, increasing a size of opening 186 may allow material 10 to be delivered from cap assembly 160' at a greater flow rate. In other examples, a portion of distal face 164' disposed about perforations 166' and/or weakened portions 169 may be formed of a biodegradable and/or bioabsorbable material such that distal face 164' and/or weakened portions 169 may be configured to degrade and/or be absorbed by tissue surrounding cap assembly 160'. The degradation may occur within seconds or minutes of contact between distal face 164' and tissue.

Still referring to FIG. 4A, cap assembly 160' may further define a dual-purpose reservoir 180' within a cavity of outer body 162. In other words, cap assembly 160' may omit a wall extending through the cavity such that a single, dual-purpose reservoir 180' is formed in outer body 162. Additionally, cap assembly 160' may include a movable floor 182' that is sized and shaped in accordance with a profile of reservoir 180'. It should be appreciated that movable floor 182' may be configured and operable in a substantially similar manner as movable floor 182 described above except for the differences explicitly described below.

In one example, not shown, it is contemplated that cap assembly 160' does not cover or obstruct the illumination/imaging devices of shaft 120. Alternatively, movable floor 182' may be formed of a substantially transparent material such that one or more devices (e.g., illumination device, imaging device, etc.) disposed within outer body 162 may be visible through movable floor 182'. In the embodiment, actuator 130 and mechanical rod 140 may be omitted entirely and pressurized medium source 150 (e.g., deployment mechanism) may be fluidly coupled to medical instrument 110 at port 118, such as, for example, via tube 152. Port 118 may be in fluid communication with a fluid lumen of shaft 120 which terminates at third opening 184 (FIG. 4B).

As described in further detail below, pressurized medium source 150 may be configured to deliver a pressurized medium to reservoir 180' via third opening 184. In other embodiments, mechanical rod 140 may be received within medical instrument 10 in lieu of and/or in conjunction with pressurized medium source 150 for deployment of material 10 from cap assembly 160'.

Figure 4B:
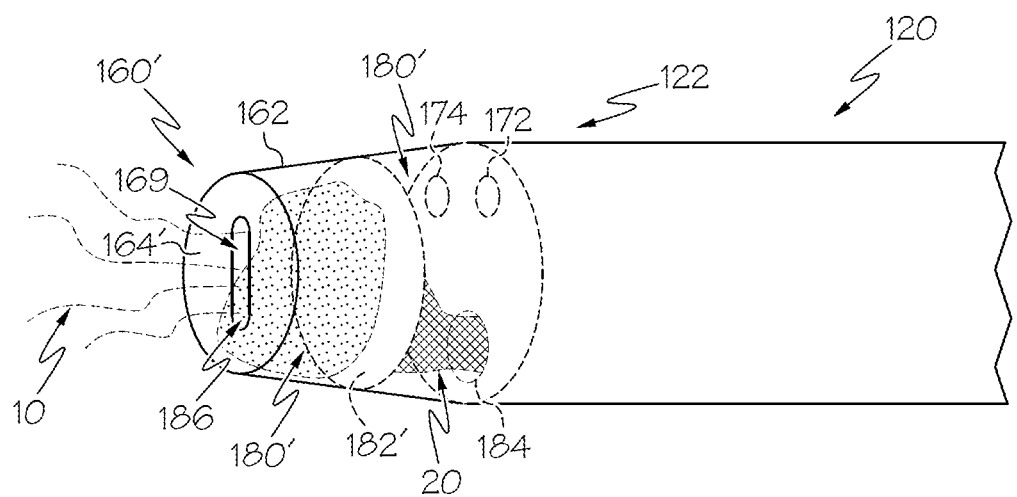
FIG. 4B is a partial perspective view of the medical instrument of FIG. 4A with the cap assembly in an expanded state, according to aspects of this disclosure.

Referring now to FIG. 4B and according to an exemplary method of using medical system 100 during a procedure with cap assembly 160', medical instrument 110 may receive cap assembly 160' by attaching outer body 162 to distal end 122. Cap assembly 160' may be preloaded with material 10 within reservoir 180' and one or more devices (e.g., illumination device, imaging device, etc.) may be coupled to medical instrument 110. Alternatively, material 10 could be inserted into material reservoir 180' through perforations 166' and/or opening 186, after cap assembly 160' is coupled to shaft 120. Shaft 120 may be inserted into a subject to position distal end 122 at a target treatment site consistent with the description above.

Upon positioning distal end 122 at the target treatment site, a user may actuate pressurized medium source 150 to deliver a pressurized medium 20 through the working channel of shaft 120 and into reservoir 180' via third opening 184. Delivery of pressurized medium 20 may cause movable floor 182' to move within reservoir 180' and toward distal face 164'. As movable floor 182' is forced toward distal face 164' at least a portion of material 10 may be delivered from cap assembly 160" via perforations 166'. Additionally, a pressure within reservoir 180' may increase when movable floor 182' moves toward distal face 164', thereby weakening a portion of outer body 162 about each perforation 166' and/or weakened portion 169.

Still referring to FIG. 4B, the portion of outer body 162 formed about perforations 166' may disintegrate (e.g., break) in response to the increased pressure applied thereto when movable floor 182' is moved within reservoir 180'. An enlarged opening 186 may be formed on distal face 164' at a location of each perforation 166' on outer body 162. Further, weakened portions 169 may disintegrate such that each opening 186 may be interconnected with one another, thereby forming a single continuous opening 186 along distal face 164'. In this instance, perforations 166' may be further enlarged to have a greater cross-sectional dimension for delivering material 10.

Accordingly, material 10 may be pushed through reservoir 180' and ejected outwardly from cap assembly 160' via opening 186. Material 10 may be delivered to the target treatment site when ejected outwardly from reservoir 180'. In some examples, perforations 166' and weakened portions 169 may comprise a relatively small portion of the surface area of distal face 164' to provide a controlled and focused application of material 10 to the target treatment site. In other examples, perforations 166' and weakened portions 169 may comprise a relatively large portion of the surface area of distal face 164' to provide a larger zone of material discharge from cap assembly 160'. In some examples, cap assembly 160' may include a plurality of perforations 166' aligned in series (e.g., in a linear configuration) on distal face 164', arranged in a matrix configuration in one or more rows and/or columns, disposed about a perimeter of distal face 164' in an annular array, or include a single large perforation 166' at a center of distal face 164'. Various other configurations and/or quantities of perforations 166' may be suitable.

Still referring to FIG. 4B, inclusion of weakened portions 169 on distal face 164' may expand a size and/or geometry of opening 186 such that additional material 10 may be delivered from cap assembly 160' at an enhanced/increased flow rate. It should be understood that, in other embodiments, additional and/or fewer perforations 166' and/or weakened portions 169 may be included on cap assembly 160' without departing from a scope of this disclosure.

For example, referring to FIG. 5A, another exemplary cap assembly 160" may include one or more perforations 166' disposed along a sidewall of outer body 162 (e.g., along an outer circumference of outer body 162). Perforations 166' may be positioned in various configurations and/or have varying geometries, such as, for example, aligned linearly and longitudinally in a series from a proximal end of cap assembly 160" (adjacent to distal end 122) to a distal end (adjacent to distal face 164'). In the example, cap assembly 160" may include four perforations 166' along the circumference of outer body 162 and longitudinally separated from one another. Although not shown, it should be understood that one or more weakened portions 169 may be included on the sidewall of outer body 162, such as, for example, longitudinally between the one or more perforations 166'.

Referring now to FIG. 5B, cap assembly 160" may be configured such that a positive pressure is generated within outer body 162 as movable floor 182' moves distally toward distal face 164'. With perforations 166' positioned on outer body 162 at varying longitudinal locations relative to one another, the pressure applied to an interior side of each perforation 166' may be dependent on a current position of movable floor 182' within reservoir 180'. For example, as movable floor 182' moves within reservoir 180' and arrives at or near a longitudinal position of a particular perforation 166', the pressure applied against an interior of said perforation 166' may cause perforation 166' to expand such that opening 186 is formed.

With the other perforations 166' positioned along other portions and/or at different lengths (longitudinal positions) of outer body 162, a pressure applied to some perforations 166' (e.g., the proximalmost perforations 166') may not or will not cause expansion of other perforations 166' (i.e., the distalmost perforations 166') positioned along other regions of outer body 162. Accordingly, it should be appreciated that at least some of the one or more perforations 166' (e.g., the distalmost perforations 166') may be maintained in an original, unexpanded state while at least some of the other perforations 166' (e.g., the proximalmost perforations 166') may be enlarged into openings 186.

In some embodiments, perforations 166' positioned adjacent to a proximal end of cap assembly 160" may include a predefined thickness that is relatively less than perforations 166' positioned adjacent to a distal end of cap assembly 160". Accordingly, perforations 166' having a smaller thickness may be configured to expand into larger openings 186 upon receipt of a smaller positive pressure than perforations 166' having a relatively greater thickness. Stated differently, perforations 166' positioned adjacent to the proximal end may break open into openings 186 or otherwise expand quicker than perforations 166' positioned adjacent to the distal end.

Still referring to FIG. 5B, a continued distal translation of movable floor 182' relative to outer body 162 may provide additional expansion of perforations 166' into openings 186. Accordingly, material 10 may be moved through reservoir 180' and delivered laterally and radially outward from cap assembly 160" in a progressive manner as additional openings 186 are enlarged/formed on outer body 162. It should be understood that a pressure applied against each perforation 166' may be greatest when a position of movable floor 182' relative to outer body 162 is substantially radially aligned with a location of the particular perforation 166' on a sidewall of outer body 162. It should further be appreciated that additional perforations 166' may be expanded as movable floor 182' continues to move relative to outer body 162.

In some embodiments, perforations 166' may have a size and/or shape that is sufficiently sized to inhibit release of material 10 from reservoir 180' absent a delivery force applied to material 10, such as, for example, by movement of movable floor 182'. In the example, perforations 166' are not configured and/or operable to be enlarged (e.g., break open, dissolve, disintegrate, etc.) and instead material 10 may be forced through perforations 166' as a pressure within reservoir 180' increases. Accordingly, larger opening(s) 186 may not be formed at a location of perforations 166' as a positive pressure is formed within reservoir 180' (e.g., when movable floor 182' translates relative to outer body 162).

In this instance, material 10 is delivered through perforations 166' and a flow rate and/or quantity of material 10 is controlled by the original size and/or shape of an opening formed by perforations 166'. In the embodiment, material 10 may have a generally high viscosity such that release of material 10 through the small perforations 166' is inhibited without a pushing force applied thereto by movable floor 182'. In other words, material 10 may not be deliverable from reservoir 180' absent movable floor 182' forcibly applying material 10 against perforations 166'.

Each of the aforementioned systems, devices, assemblies, and methods may be used to provide a material adjacent a target treatment site in a subject (e.g., a patient), while the material is sealed in a cap assembly, and deploy the material from the cap assembly to the target treatment site within the subject. By providing a medical device including a cap assembly having one or more removable seals or perforations, a user may selectively deploy the material from the device during a procedure. In this instance, a user may reduce overall procedure time, increase efficiency of procedures, and/or avoid unnecessary harm to a subject's body caused by the medical instrument inadvertently releasing the material or requiring introduction of additional devices to deploy the sealed material.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device, comprising:
   a shaft having a distal end, wherein the distal end includes an opening and an imaging device;
   a cap at the distal end of the shaft, wherein the cap defines a first reservoir for storing a material and a second reservoir, wherein the second reservoir is aligned with the imaging device such that the imaging device is able to capture images distally of the cap through a distal face of the cap, and wherein the first reservoir is misaligned from the imaging device, such that the imaging device is isolated from the material stored in the first reservoir; and
   a deployment mechanism configured to eject the material from the first reservoir, wherein the deployment mechanism includes a movable floor that is distal of the distal end of the shaft, wherein the movable floor is configured to apply a force to the material in the first reservoir, wherein the movable floor includes a protrusion that is received within the opening of the distal end of the shaft;
   wherein the cap includes a seal, wherein the seal is configured to contain the material in the first reservoir in an absence of the force applied by the deployment mechanism to the material.

2. The medical device of claim 1, wherein the deployment mechanism further includes a movable rod disposed within the shaft and extendable from the distal end of the shaft.

3. The medical device of claim 2, wherein the movable rod is configured to push the movable floor distally away from the distal end of the shaft to eject the material from the first reservoir.

4. The medical device of claim 2, wherein the protrusion of the movable floor is configured to align the movable floor with the movable rod.

5. The medical device of claim 1, wherein the deployment mechanism includes a source of pressurized medium, wherein the pressurized medium is configured to be delivered through the shaft from the source of pressurized medium, wherein delivery of the pressurized medium moves movable floor distally to apply the force to the material.

6. The medical device of claim 1, wherein the seal includes a movable cover coupled to the cap, wherein the movable cover is configured to move to form an opening through which the material is able to exit the cap.

7. The medical device of claim 6, further including an actuator, wherein a distal end of the actuator is coupled to the movable cover, wherein actuation of the actuator is configured to move the movable cover to form the opening.

8. The medical device of claim 7, wherein the actuator includes a wire, a cable, or a thread, and wherein the actuator is configured to move the movable cover in response to a proximal pulling force being exerted on the actuator.

9. The medical device of claim 7, wherein the distal end of the actuator is coupled to an exterior surface of the movable cover, and wherein the actuator extends proximally along an external surface of the shaft.

10. The medical device of claim 1, wherein an outer surface of the cap includes a biodegradable material that is configured to degrade within seconds or minutes of contact with tissue.

11. The medical device of claim 1, wherein the protrusion is sized and shaped in accordance with a profile of the opening of the distal end of the shaft, and wherein a distal portion of the movable floor is wider than (a) the opening of the distal end of the shaft and (b) the protrusion.

12. The medical device of claim 1, wherein the first reservoir is isolated from the second reservoir by a wall that extends from a proximalmost end of the cap to a distalmost end of the cap.

13. The medical device of claim 1, wherein the movable floor is isolated from the second reservoir.

14. A medical device, comprising:
   a cap configured to be attached to a distal end of a scope, wherein the cap defines a first reservoir for storing a material, and a second reservoir, wherein the second reservoir is isolated from the first reservoir by a wall, wherein the wall extends from a proximalmost end of the cap to a distalmost end of the cap, wherein the cap includes:
   a removable seal configured to expose the first reservoir and the material upon removal of the seal from a remainder of the cap; and a deployment mechanism configured to eject the material from the first reservoir, wherein the deployment mechanism includes:
a movable floor, wherein the movable floor is distal of the distal end of the scope, wherein the movable floor is configured to generate a positive pressure within the first reservoir as the movable floor moves distally within the first reservoir; and
a protrusion, wherein the protrusion is received within an opening of the distal end of the scope.

15. The medical device of claim 14, wherein the removable seal is formed of biodegradable material such that the removable seal is configured to degrade upon exposure to a target site for a predetermined duration.

16. The medical device of claim 14, wherein the movable floor is isolated from the second reservoir.

17. A medical device, comprising:
a cap configured for attachment to a distal end of a shaft of a scope, wherein the cap defines a first reservoir for storing a material and a second reservoir, wherein the second reservoir is isolated from the first reservoir by a wall and extends from a proximalmost end of the cap to a distalmost end of the cap, wherein the cap includes a deployment mechanism configured to eject the material from the first reservoir, wherein the deployment mechanism includes:
a movable floor that is distal to the distal end of the scope, wherein the movable floor is configured to apply a force to the material in the first reservoir, wherein the movable floor includes a protrusion on a proximal surface of the movable floor, wherein the protrusion is received within an opening of the distal end of the scope, and wherein the movable floor is isolated from the second reservoir; and
a movable rod, wherein the movable rod is disposed within a lumen of the shaft and extendable from the distal end of the scope, wherein the protrusion of the movable floor is configured to align the movable rod with the movable floor.

18. The medical device of claim 17, wherein the protrusion is sized and shaped in accordance with a profile of the opening of the distal end of the shaft, and wherein a distal portion of the movable floor is wider than (a) the opening of the distal end of the shaft and (b) the protrusion.

19. The medical device of claim 17, wherein the wall extends from a proximalmost end of the cap to a distalmost end of the cap.

20. The medical device of claim 17, wherein the second reservoir is configured to align with at least a first opening within a visualization device disposed to the distal end of the scope, and wherein the first reservoir is aligned to a third opening positioned away from the first opening.

* * * * *